(12) United States Patent
Levi

(10) Patent No.: US 10,201,701 B2
(45) Date of Patent: Feb. 12, 2019

(54) ORAL ELECTRICAL CLEANING DEVICE

(71) Applicant: BenZion Levi, Habonim (IL)

(72) Inventor: BenZion Levi, Habonim (IL)

(73) Assignee: Home Skinovations Ltd., Yokneam (IL)

( * ) Notice: Subject to any disclaimer, the term of this patent is extended or adjusted under 35 U.S.C. 154(b) by 215 days.

(21) Appl. No.: 15/149,272

(22) Filed: May 9, 2016

(65) Prior Publication Data

US 2017/0209692 A1    Jul. 27, 2017

Related U.S. Application Data

(60) Provisional application No. 62/139,736, filed on Mar. 29, 2015.

(51) Int. Cl.
| | |
|---|---|
| *A61N 1/26* | (2006.01) |
| *A61N 1/05* | (2006.01) |
| *A61N 1/40* | (2006.01) |
| *A61N 1/30* | (2006.01) |
| *A61N 1/20* | (2006.01) |
| *A61C 17/32* | (2006.01) |
| *A61C 19/06* | (2006.01) |
| *A61N 1/32* | (2006.01) |

(52) U.S. Cl.
CPC .............. *A61N 1/26* (2013.01); *A61C 17/32* (2013.01); *A61C 19/06* (2013.01); *A61N 1/0548* (2013.01); *A61N 1/205* (2013.01); *A61N 1/306* (2013.01); *A61N 1/322* (2013.01); *A61N 1/40* (2013.01)

(58) Field of Classification Search
CPC ........ A61N 1/26; A61N 1/0548; A61N 1/205; A61N 1/306; A61N 1/40; A61C 17/00
See application file for complete search history.

(56) References Cited

U.S. PATENT DOCUMENTS

| | | | | |
|---|---|---|---|---|
| 7,947,037 | B1 * | 5/2011 | Garito | ............ A61B 18/14 |
| | | | | 606/32 |
| 9,811,636 | B2 * | 11/2017 | Dykes | ............ G06F 19/345 |
| 2006/0070195 | A1 * | 4/2006 | Morita | ............ A46B 15/0016 |
| | | | | 15/105 |
| 2017/0360973 | A1 * | 12/2017 | Saue | ............ A61L 2/14 |

FOREIGN PATENT DOCUMENTS

| | | |
|---|---|---|
| EP | 0357852 | 3/1990 |
| EP | 2617319 | 7/2013 |
| JP | 2007-167527 | 7/2007 |

OTHER PUBLICATIONS

PCT Search Report and Written Opinion PCT/IB2016/053501, dated Mar. 1, 2017.

* cited by examiner

*Primary Examiner* — Shay Karls

(74) *Attorney, Agent, or Firm* — Dekel Patent Ltd.; David Klein

(57) ABSTRACT

An oral cleaning device includes a head portion that supports cleaning elements, a handle portion extending from the head portion, an RF generator disposed in the handle portion, connected to electrodes located on the head portion, and additionally or alternatively, a microcurrent source disposed in the handle portion, connected to a conductive surface located on the handle and to one of the electrodes located on the head portion, and a non-conductive barrier located on the head portion that separates the electrodes from each other.

14 Claims, 4 Drawing Sheets

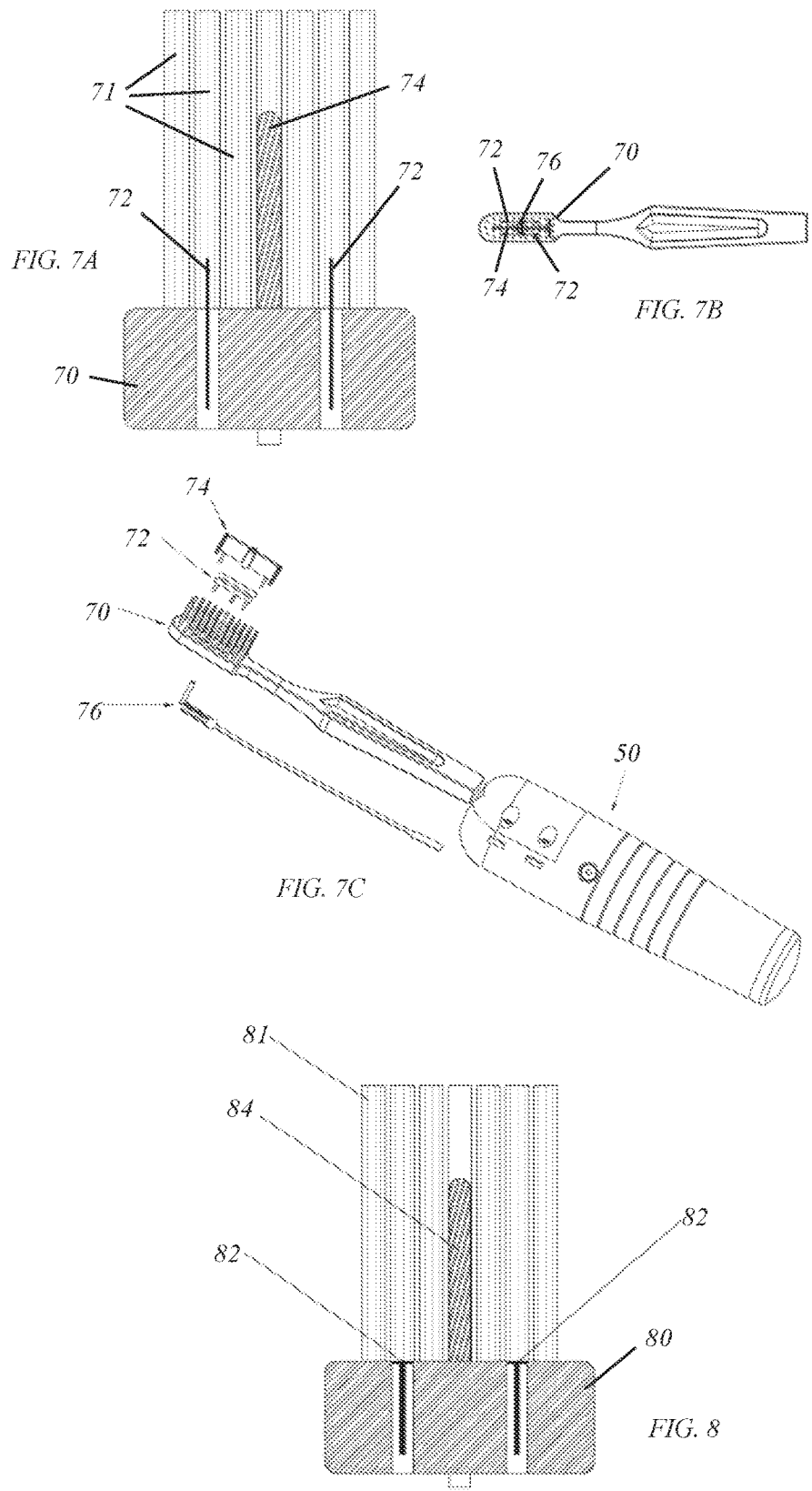

ORAL ELECTRICAL CLEANING DEVICE

FIELD OF THE INVENTION

The present invention relates generally to oral cleaning devices, and particularly to an oral cleaning device, such as a toothbrush, that generates a chemical agent in situ by applying RF energy to electrodes on the cleaning device in the presence of substances in the user's mouth.

BACKGROUND OF THE INVENTION

Oral care products include a variety of chemical agents that perform a range of functions. For instance, toothpastes, mouthwashes and whiteners include chemical agents that help to clean teeth, kill bacteria, freshen breath and/or whiten teeth. These products typically cooperate with a device such as a toothbrush, an applicator device, or a tongue scraper, to perform their intended functions. In addition, chemical agents in these products may provide secondary benefits such as providing pleasing flavors or odors.

Oral care products that are directed to whitening teeth include an oxidizing agent as the primary active ingredient, such as hydrogen peroxide. These products are formulated into liquids, pastes or gels for application to the teeth. Upon storage, these products lose their whitening efficacy over time. In addition, these products have a brief period of efficacy when applied to the teeth in the oral cavity. For example, saliva contains high concentrations of the enzyme catalase, which on contact rapidly decomposes hydrogen peroxide into gaseous oxygen and water and so that there is only transitory contact of the peroxide whitening agent with the teeth. In addition, the low viscosities of aqueous peroxide solutions do not allow the peroxide whitening agent to remain in contact with the teeth for as long as is necessary to effect substantive whitening, because of the constant flushing effects of salivary secretions. As such, it is desirable to have high concentrations of oxidizing agents or effective oxidizing agents applied directly to teeth.

U.S. Pat. No. 8,156,602 to Jiminez et al. describes a device for generating a chemical agent in situ on an as-needed basis via the application of an electrical potential across a pair of conductors in communication with an electrolyte. The device is a toothbrush that generates chemical agents in a user's mouth by applying an electrical potential to an electrolyte such as saliva and/or a dentifrice located therein. The chemical agents include ozone, hydrogen peroxide, peroxide, chlorine and/or hypochlorite. The toothbrush includes a voltage source and a first set of electrodes for applying an electrical potential to the electrolyte. The toothbrush includes a second set of electrodes disposed about an anode of the first set of electrodes. The first and second sets of anodes cooperate to produce ions, peroxides, ozone and/or other chemical agents via the application of electrical potential to the electrolyte.

SUMMARY OF THE INVENTION

The present invention seeks to provide an oral cleaning device, such as a toothbrush, that generates a chemical agent in situ by applying RF energy and/or microcurrent source to a conductive surface and/or to electrodes on the cleaning device in the presence of substances in the user's mouth, as is described more in detail hereinbelow.

There is thus provided in accordance with an embodiment of the present invention an oral cleaning device including a head portion that supports cleaning elements, a handle portion extending from the head portion, an RF generator disposed in the handle portion, connected to electrodes located on the head portion, and a non-conductive barrier located on the head portion that separates the electrodes from each other. Alternatively or additionally, a microcurrent source is disposed in the handle portion, connected to a conductive surface located on the handle and to one of the electrodes located on the head portion.

In accordance with an embodiment of the present invention a voltage source in the handle portion is connected to the RF generator and to the microcurrent source.

In accordance with an embodiment of the present invention the electrodes are located at opposite sides of the head portion.

In accordance with an embodiment of the present invention the conductive surface is on the outside surface of the handle.

In accordance with an embodiment of the present invention the cleaning elements are located between the non-conductive barrier and each of the electrodes.

In accordance with an embodiment of the present invention the cleaning elements surround the non-conductive barrier.

In accordance with an embodiment of the present invention the microcurrent source, conductive surface and the electrodes operate in a galvanic mode.

In accordance with an embodiment of the present invention the RF generator and the electrodes operate in a bipolar mode.

In accordance with an embodiment of the present invention the RF generator, the microcurrent source, the conductive surface and the electrodes operate in a combination of bipolar and galvanic modes

BRIEF DESCRIPTION OF THE DRAWINGS

The present invention will be understood and appreciated more fully from the following detailed description, taken in conjunction with the drawings in which:

FIGS. 7A-7C are simplified illustrations of a bristle head portion with electrodes and a non-conductive barrier between them, according to an additional non-limiting embodiment of the invention, wherein FIG. 7A is a side view of the head portion, FIG. 7B is a top view of the brush and FIG. 7C is an exploded view of the brush.

FIG. 8 is a side view of a bristle head portion with electrodes and a non-conductive barrier between them, according to an additional non-limiting embodiment of the invention.

DETAILED DESCRIPTION OF EMBODIMENTS

Figure 1:
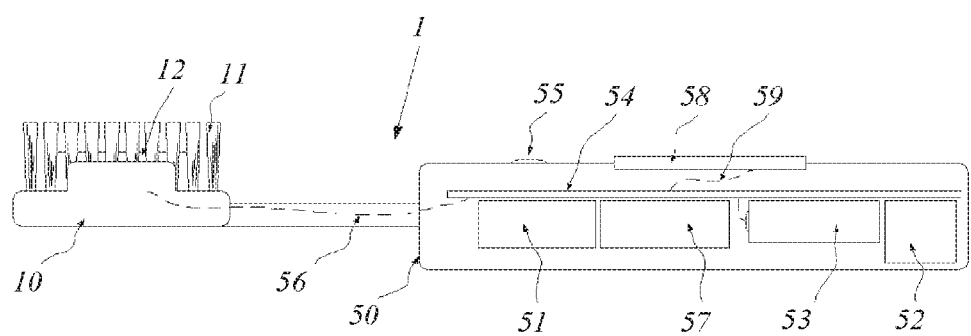
FIG. 1 is a perspective side view illustration of an oral cleaning device, e.g., a toothbrush, in accordance with a non-limiting embodiment of the invention.

Reference is now made to FIG. 1, which illustrate an oral cleaning device 1, constructed and operative in accordance with a non-limiting embodiment of the present invention.

Device 1 includes a head portion 10 at one end supporting cleaning elements such as bristles 11, and a handle portion 50 at the opposite end. The handle portion 50 may house therein a voltage source 53, such as a battery (e.g., rechargeable). A battery charger 52 may also be provided in handle portion 50 for recharging battery 53. An RF (radio frequency energy) generator 51 is provided in handle portion 50, powered by voltage source (battery) 53, for generating RF energy in a frequency range, typically but not limited to, 500 KHz-30 MHz. Alternatively or additionally, a microcurrent source 57 is provided in handle portion 50, powered by voltage source (battery) 53, for generating galvanic energy in a current range, typically but not limited to 50 microamperes to 250 microamperes and frequency range, typically but not limited to, 1 Hz-500 Hz. All these components may be mounted on a printed circuit board 54 and operated with one or more control buttons 55. The PCB 54 may also comprise control circuitry for controlling the operation of the RF generator 51, microcurrent source 57 or the control circuitry may be built in to RF generator 51 and/or to microcurrent source 57.

Figure 2:
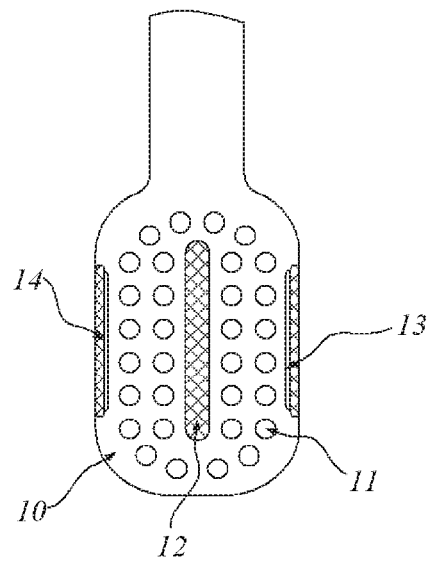
FIG. 2 is a close-up, front view illustration of a bristle head portion of the device, in accordance with a non-limiting an embodiment of the invention.
Figure 3:
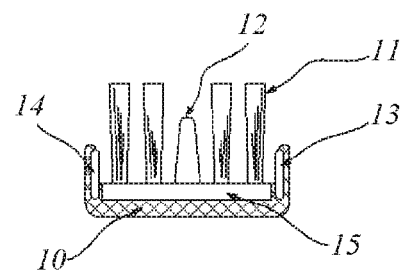
FIG. 3 is a close-up, side view illustration of a bristle head portion of the device, in accordance with a non-limiting an embodiment of the invention.

The RF generator 51 is electrically connected to electrodes 13 and 14 (seen in FIG. 2) via RF connecting wires 56. The electrodes 13 and 14 are located at opposite sides of head portion 10 and are separated by a non-conductive barrier 12. Bristles 11 are located between the non-conductive barrier 12 and each of the electrodes 13 and 14. As seen in FIG. 2, bristles 11 may surround the non-conductive barrier 12. As seen in FIG. 3, bristles 11 may be mounted on a replaceable case 15.

The microcurrent source 57 is electrically connected to electrode 13 (seen in FIG. 2) and to conductive surface 58 via RF connecting wires 56 and microcurrent connecting wires 59. The conductive surface 58 is located on the outer surface of the handle portion 50.

The electrodes 13 and 14 are also referred to as first RF pole 13 and second RF pole 14, respectively.

The electrode 13 and the conductive surface 58 are also referred to as first microcurrent pole 13 and second microcurrent pole 58, respectively.

The electrodes 13 and 14 as RF poles are able to make contact with an electrolyte within a user's mouth and generate chemical agents in situ at the application site of the agents. The electrode 13 as microcurrent pole is able to make a contact with an electrolyte within a user's mouth and a conductive surface 58 as microcurrent pole is able to make a contact with the user's body and generate chemical agents in situ at the application site of the agents. The electrolyte may include saliva alone, a dentifrice in the presence of saliva, and/or a mixture of saliva, dentifrice and conductivity agents, such as salts, which increase the conductivity of an aqueous solution.

Although shown as a toothbrush with a non-moving head, it is understood that device 1 could have a moving head and may have a variety of configurations.

The RF generator 51 is electrically connected to electrodes 13 and 14 for providing RF energy to the electrodes 13 and 14. The microcurrent source 57 is electrically connected to electrode 13 and to conductive surface 58 for providing galvanic energy to electrode 13 and conductive surface 58. The electrodes 13, 14 and conductive surface 58 may operate in a galvanic mode, bipolar mode or a combination of galvanic and bipolar modes. The RF and galvanic energies enhance the efficacy of the chemical agents in the user's mouth.

Device 1 can generate the chemical agents in a variety of ways depending on factors such as the configuration of the toothbrush, the RF energy (such as but not limited to, frequency 1 MHz and amplitude 11V peak) provided to the electrodes and the galvanic energy (such as but not limited to, frequency 10 Hz and microcurrent of 50 microamperes) provided to the electrode and the conductive surface, the composition of the electrolyte, the composition of the electrodes and other factors. For instance, in the presence of saliva alone, device 1 can generate hydrogen, oxygen, peroxide and ozone; in the presence of ionic compounds such as sodium chloride, potassium chloride, or calcium carbonate that may be contained in an aqueous dentifrice, chemical agents such as chlorine or calcium can be generated; in another example, in the presence of a dentifrice containing an activatable chemical agent that is stored in an inactive state, the chemical agent can be generated by being activated via the RF energy and/or galvanic energy.

Many configurations of the RF poles and bristles (cleaning elements) can be made in accordance with the invention. Non-limiting examples are given in FIGS. 4-6.

Figure 4:
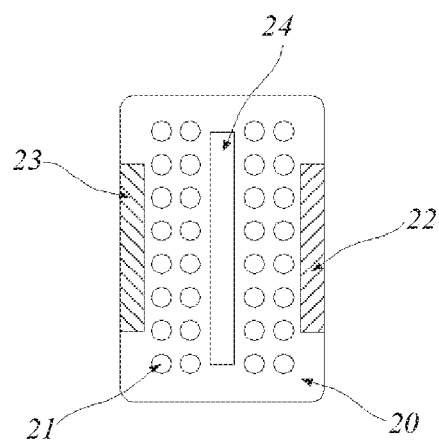
FIG. 4 is a front view illustration of a bristle head portion with two electrodes and a non-conductive barrier between them, according to an additional non-limiting embodiment of the invention.

FIG. 4 illustrates an embodiment of a head portion 20 with two RF electrodes 22 and 23 and a non-conductive barrier 24 between them. Bristles 21 are located between the non-conductive barrier 24 and each of the electrodes 22 and 23.

Figure 5:
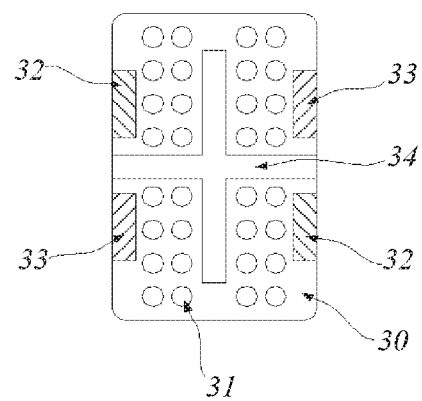
FIG. 5 is a front view illustration of a bristle head portion with four electrodes and a non-conductive barrier between them, according to an additional non-limiting embodiment of the invention.

FIG. 5 illustrates an embodiment of a head portion 30 with four RF electrodes (two pairs of electrodes 32 and 33) and a non-conductive barrier 34 between each of the electrodes. In the illustrated embodiment, barrier 34 is a cross-shaped barrier that separates all the electrodes from each other. Bristles 31 are located between the non-conductive barrier 34 and each of the electrodes 32 and 33.

Figure 6:
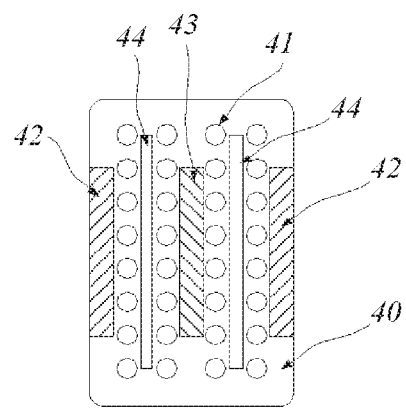
FIG. 6 is a front view of a bristle head portion with three electrodes and a non-conductive barrier between them, according to an additional non-limiting embodiment of the invention.

FIG. 6 illustrates an embodiment of a head portion 40 with three RF electrodes (two outer electrodes 42 and an intermediate electrode 43) and non-conductive barriers 44 between intermediate electrode 43 and each of the outer electrodes 42. Bristles 41 are located between the non-conductive barriers 44 and each of the electrodes 42 and 43.

FIGS. 7A-7C illustrate an embodiment of a head portion 70 with RF electrodes 72 (two electrodes are shown but the invention is not limited to just two electrodes) and a non-conductive barrier 74 between the electrodes 72 (if more than two electrodes are used then more than one non-conductive barrier may be used). Bristles (cleaning elements) 71 are located between the non-conductive barrier 74 and each of the electrodes 72.

In this embodiment, as well as any of the other embodiments, a temperature sensor 76 may be located on the head portion 70 and/or the non-conductive barrier 74. The temperature sensor 76 may be in communication with the control circuitry for controlling the operation of the RF generator (shown in FIG. 1) located in handle portion 50. The temperature sensor 76 may serve as a safety feature that senses the toothpaste temperature during the treatment. If the temperature rises above a non-safe temperature (e.g., 41° C.), then the sensor 76 turns off the RF energy.

FIG. 8 illustrates an embodiment of a head portion 80 with RF electrodes 82 (two electrodes are shown but the invention is not limited to just two electrodes) and a non-conductive barrier 84 between the electrodes 82 (if more than two electrodes are used then more than one non-conductive barrier may be used). Bristles (cleaning elements) 81 are located between the non-conductive barrier 84 and each of the electrodes 82. The electrodes 82 are flush with the head portion 80 so that they do not protrude in between the bristles 81.

The different heights of the electrodes in the illustrated embodiments create different electrical and electromagnetic fields in the vicinity of the brush head and barrier.

What is claimed is:

1. An oral cleaning device comprising:
    a head portion comprising cleaning elements which are bristles;
    a handle portion extending from said head portion;
    an RF (radio frequency energy) generator disposed in said handle portion, connected to electrodes located on said head portion; and
    a non-conductive barrier, which is not a bristle, located on said head portion that separates said electrodes from each other.
2. The oral cleaning device according to claim 1, further comprising a microcurrent source disposed in said handle portion, connected to one of the electrodes on said head portion and to a conductive surface located on the handle.
3. The oral cleaning device according to claim 2, comprising a voltage source in said handle portion connected to said microcurrent source.
4. The oral cleaning device according to claim 2, wherein said conductive surface is located at the outer surface of said handle portion.
5. The oral cleaning device according to claim 2, wherein said microcurrent source and said electrodes and said conductive surface operate in a galvanic mode.
6. The oral cleaning device according to claim 2, wherein said RF generator, said microcurrent source, said conductive surface and said electrodes operate in a combination of galvanic and bipolar modes.
7. The oral cleaning device according to claim 1, comprising a voltage source in said handle portion connected to said RF generator.
8. The oral cleaning device according to claim 1, wherein said electrodes are located at opposite sides of said head portion.
9. The oral cleaning device according to claim 1, wherein said cleaning elements are located between said non-conductive barrier and each of said electrodes.
10. The oral cleaning device according to claim 1, wherein said cleaning elements surround said non-conductive barrier.
11. The oral cleaning device according to claim 1, wherein said RF generator and said electrodes operate in a bipolar mode.
12. The oral cleaning device according to claim 1, wherein said electrodes do not protrude in between said cleaning elements.
13. The oral cleaning device according to claim 1, further comprising a temperature sensor located on said head portion and/or said non-conductive barrier.
14. The oral cleaning device according to claim 1, wherein said non-conductive barrier is at least half the height of said cleaning elements.

* * * * *